(12) United States Patent
Uemura (10) Patent No.: US 9,557,751 B2
(45) Date of Patent: Jan. 31, 2017

(54) SENSOR TEMPERATURE CONTROL APPARATUS

(71) Applicant: NGK SPARK PLUG CO., LTD., Nagoya-shi, Aichi-ken (JP)

(72) Inventor: Tomonori Uemura, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 486 days.

(21) Appl. No.: 14/226,407

(22) Filed: Mar. 26, 2014

(65) Prior Publication Data

US 2014/0291410 A1 Oct. 2, 2014

(30) Foreign Application Priority Data

Mar. 27, 2013 (JP) ................. 2013-067190

(51) Int. Cl.
*F23N 5/20* (2006.01)
*G05D 23/00* (2006.01)
*G05D 23/19* (2006.01)
*G01N 27/406* (2006.01)

(52) U.S. Cl.
CPC ...... *G05D 23/1919* (2013.01); *G01N 27/4067* (2013.01)

(58) Field of Classification Search
CPC .......... G05D 23/1919; G01N 27/4067
See application file for complete search history.

(56) References Cited

U.S. PATENT DOCUMENTS

2002/0179443 A1* 12/2002 Hada ............... F02D 41/1494
                                                        204/408
2004/0089060 A1* 5/2004 Suzuki ............... G01N 27/4175
                                                        73/114.73

FOREIGN PATENT DOCUMENTS

JP       2000-292411 A     10/2000

* cited by examiner

*Primary Examiner* — Lisa Caputo
*Assistant Examiner* — Janice M Soto
(74) *Attorney, Agent, or Firm* — Sughrue Mion, PLLC (57) ABSTRACT

A sensor temperature control apparatus (1) includes switching device (51); energization control means S1 and S2 for controlling duty ratio DT to maintain sensor element section (3) at a target temperature; storage means (75) for storing a first duty ratio DT1 in advance; element temperature judgment means S3 for determining whether the temperature of the sensor element section falls within a first temperature range including the target temperature; and semi-shorted state detection means S4 to S6 for comparing a present duty ratio DT2 with the first duty ratio in a state in which the temperature of the sensor element section falls within the first temperature range, to thereby determine whether a semi-shorted first temperature range state has arisen in which only a portion of the current flowing through switching device flows through heater section (4) and the temperature of the sensor element section falls within the first temperature range.

4 Claims, 4 Drawing Sheets

SENSOR TEMPERATURE CONTROL APPARATUS

TECHNICAL FIELD

The present invention relates to a sensor temperature control apparatus used for a sensor having a sensor element section and a heater section so as to control the temperature of the sensor element section by controlling pulse energization of the heater section (i.e., energization of the heater section through application voltage pulses thereto).

BACKGROUND ART

A conventionally known example of a sensor having a sensor element section and a heater section is a gas sensor which detects the concentration of a specific gas contained in exhaust gas, such as an oxygen sensor or a nitrogen oxide ($NO_x$) sensor. These gas sensors include a sensor element section which is formed of a solid electrolyte body whose main component is zirconia, and a heater section which heats the sensor element section so as to bring it into an activated state. In order to bring the sensor element section into an activated state, a sensor temperature control apparatus controls the pulse energization of the heater section to thereby control the temperature of the sensor element section.

The sensor temperature control apparatus includes a switching device for on-off controlling the supply of electricity to the heater section, and feedback-controls the duty ratio of energization control pulses input to the switching device such that the sensor element section is heated to a target temperature.

Notably, switching devices used for the sensor temperature control apparatus are categorized into a high-side-type switching device which is interposed between a power supply (power supply potential) and the heater section, and a low-side-type switching device which is interposed between the heater section and a ground potential. For example, Patent Document 1 discloses a gas concentration detection apparatus which uses a gas concentration sensor and whose heater control circuit includes a high-side-type switching device (switch) (FIG. 10) or a low-side-type switching device (switch) (FIG. 11).

PRIOR ART DOCUMENT

Patent Document

[Patent Document 1] Japanese Patent Application Laid-Open (kokai) No. 2000-292411

SUMMARY OF THE INVENTION

Problem to be Solved by the Invention

Incidentally, in such a sensor temperature control apparatus, a connection path which connects the heater section and the switching device may contact and communicate with a portion having the ground potential or the power supply potential, to thereby form a so-called short-circuit. In the sensor temperature control apparatus in which a high-side-type switching device is employed, such a short circuit is formed when a cable which connects the heater section and the switching device contacts and communicates with a member having the ground potential. In the sensor temperature control apparatus in which a low-side-type switching device is employed, such a short circuit is formed when the cable which connects the heater section and the switching device contacts and communicates with a member having the power supply potential. If energization of the heater section is continued in a state in which such a short circuit is formed, energy may be wasted, and the switching device may fail. Therefore, the sensor temperature control apparatus is demanded to properly detect formation of such a short circuit.

However, when such a short circuit is formed, the resistance of the short circuit between the member having the ground potential or the power supply potential and the connection path which connects the heater section and the switching device is not necessarily low, and the connection path communicates with the member having the ground potential or the power supply potential through a short circuit whose resistance may be somewhat large because of presence of contact resistance and wiring resistance. In such a state, when the switching device is turned on, only a portion of the current flowing through the switching device flows through the heater section, the remaining portion of the current flows through the short circuit having a resistance. When the sum of the current flowing through the heater section and the current flowing through the short circuit reaches the upper limit of the current which can flow through the switching device, the current flowing through the switching device is restricted, and the voltage drop across the switching device increases, whereby the voltage applied to the heater section decreases.

In such a case, the sensor temperature control apparatus increase the duty ratio of energization control pulses input to the switching device through feedback control. Therefore, if the decrease in the voltage applied to the heater section is small, the electric power supplied to the heater section is maintained in a state in which the short circuit having a resistance is still formed. In such a case, the temperature of the sensor element section can be maintained at a temperature near a predetermined target temperature. Namely, in such a case, despite the formation of a short circuit having a resistance, it cannot be detected as an anomaly from the temperature of the sensor element section. Therefore, in some situations, the temperature control for the sensor is continued in a state in which the short circuit having a resistance still exists.

The present invention has been accomplished in view of the above-mentioned problem, and provides a sensor temperature control apparatus which can properly detect a state in which a sensor element section is maintained at a temperature near a target temperature even though only a portion of the current flowing through a switching device flows through a heater section.

Means for Solving the Problems

One mode of the present invention is a sensor temperature control apparatus used for a sensor having a sensor element section and a heater section for heating the sensor element section and adapted to control the temperature of the sensor element section by controlling pulse energization of the heater section. The sensor temperature control apparatus comprises a switching device which allows and prohibits supply of electricity to the heater section; energization control means for feedback-controlling a duty ratio of an energization control pulse signal input to the switching device such that the sensor element section is maintained at a target temperature; storage means for storing in advance a first duty ratio which is the duty ratio in an un-shorted constant temperature state in which all current flowing through the switching device flows through the heater section and the sensor element section is maintained at the target temperature; element temperature judgment means for determining whether or not the temperature of the sensor element section falls within a first temperature range including the target temperature; and semi-shorted state detection means for comparing a present duty ratio which is the duty ratio at present with the previously stored first duty ratio in a state in which the temperature of the sensor element section falls within the first temperature range, to thereby determine whether or not there has arisen a semi-shorted first temperature range state in which only a portion of the current flowing through the switching device flows through the heater section and the temperature of the sensor element section falls within the first temperature range.

As described above, when the connection path which connects the heater section and the switching device is shorted to the ground potential or the power supply potential through a short circuit having a resistance and the voltage applied to the heater section decreases, feedback control increases the duty ratio of the energization control pulse input to the switching device. Therefore, in the semi-shorted first temperature range state in which the temperature of the sensor element section falls within the first temperature range including the target temperature even though only a portion of the current flowing through the switching device flows through the heater section due to formation of a short circuit having a resistance (hereinafter this state will be referred to as a "semi-shorted state"), the duty ratio of the energization control pulse becomes large, as compared with an un-shorted constant temperature state in which all the current flowing through the switching device flows through the heater section and the sensor element section is maintained at the target temperature.

In view of this, in the present sensor temperature control apparatus, a first duty ratio which is the duty ratio in the un-shorted constant temperature state is stored in the storage means in advance.

The determination as to whether there has arisen the semi-shorted first temperature range state is made by comparing the present duty ratio with the first duty ratio in a state in which the temperature of the sensor element section falls within the first temperature range.

As a result, it is possible to properly detect a state in which the temperature of the sensor element section is maintained at a temperature near the target temperature even though only a portion of the current flowing through the switching device flows through the heater section due to formation of a short circuit having a resistance.

Examples of the switching device include discrete switching devices such as power transistor, power MOSFET, and IGBT, and an IPD (Intelligent Power Device) in which a protection circuit for over current or over voltage or the like is integrated together with a switching device. These switching devices are categorized into a high-side-type switching device which is interposed between the power supply potential and the heater section and a low-side-type switching device which is interposed between the heater section and the ground potential. The high-side-type switching device and the low-side-type switching device differ from each other in terms of the manner in which a short circuit is formed.

An example of the method for feedback-controlling the energization of the heater section by using the energization control means such that the sensor element section is maintained at the target temperature is a method which is used for a sensor whose sensor element section has a characteristic that its element resistance changes with the temperature of the sensor element section, the method detecting the element resistance of the sensor element section and performing feedback control such that the detected element resistance becomes equal to a target resistance corresponding to the target temperature.

Another method is detecting the element temperature of the sensor element section by a temperature sensor and performing feedback control such that the detected element temperature becomes equal to a predetermined temperature.

The first duty ratio stored in the storage means may be a fixed duty ratio which is stored in advance as the first duty ratio and is used continuously. Alternatively, the first duty ratio stored in the storage means may be a duty ratio in the un-shorted constant temperature state which is obtained in the previous operation, is stored as the first duty ratio, and is used at the time of the next operation. Use of the duty ratio at the time of the previous operation allows the first duty ratio to change in accordance with a change in the element resistance, which change occurs due to deterioration or the like.

An example of the specific determination method which is employed by the semi-shorted state detection means so as to determine whether or not the semi-shorted first temperature range state has arisen by comparing the present duty ratio with the first duty ratio is a method of subtracting the first duty ratio from the present duty ratio and determining whether or not the resultant value is greater than a predetermined threshold value. Another method is calculating the ratio of the present duty ratio to the first duty ratio and determining whether or not the calculated ratio is greater than a predetermined threshold value.

In the above-described sensor temperature control apparatus, preferably, the switching device is a high-side-type switching device interposed between a power supply potential and the heater section; and the semi-shorted state detection means includes first judgment means for determining, by comparing the present duty ratio with the first duty ratio, whether or not a first connection path which connects the switching device and a power-supply-side terminal of the heater section communicates with a ground potential through a resistive short circuit having a resistance, and the semi-shorted first temperature range state has arisen.

In this sensor temperature control apparatus, the switching device is a high-side-type switching device. The semi-shorted state detection means includes the first judgment means, and determining, by comparing the present duty ratio with the first duty ratio, whether or not the sensor, the sensor temperature control apparatus, and the resistive short circuit are in the semi-shorted first temperature range state. As a result, occurrence of the semi-shorted first temperature range state can be properly determined in a sensor temperature control apparatus in which a high-side type switching device is employed.

In the above-described sensor temperature control apparatus, preferably, the switching device is a low-side-type switching device interposed between the heater section and a ground potential; and the semi-shorted state detection means includes second judgment means for determining, by comparing the present duty ratio with the first duty ratio, whether or not a second connection path which connects a ground-side terminal of the heater section and the switching device communicates with a power supply potential through a resistive short circuit having a resistance, and the semi-shorted first temperature range state has arisen.

In this sensor temperature control apparatus, the switching device is a low-side-type switching device. The semi-shorted state detection means includes the second judgment means, and determining, by comparing the present duty ratio with the first duty ratio, whether or not the sensor, the sensor temperature control apparatus, and the resistive short circuit are in the semi-shorted first temperature range state. As a result, occurrence of the semi-shorted first temperature range state can be properly determined in a sensor temperature control apparatus in which a low-side type switching device is employed.

In any of the above-described sensor temperature control apparatuses, preferably, the sensor element section has a characteristic that its element resistance changes with its temperature; the energization control means includes element resistance detection means for detecting the element resistance of the sensor element section, and element resistance control means for feedback-controlling the duty ratio such that the detected element resistance becomes equal to a target resistance; the element temperature judgment means is element resistance judgment means for determining whether or not the element resistance falls within a first resistance range including the target resistance; and the semi-shorted state detection means is means for determining whether or not the semi-shorted first temperature range state has arisen by comparing the present duty ratio with the first duty ratio in a state in which the element resistance falls within the first resistance range.

In this sensor temperature control apparatus, the energization control means includes element resistance detection means and element resistance control means, and the semi-shorted state detection means determines whether or not the semi-shorted first temperature range state has arisen, in a state in which the element resistance falls within the first resistance range.

Therefore, it is possible to properly detect the semi-shorted first temperature range state through use of the element resistance.

MODE FOR CARRYING OUT THE INVENTION

First Embodiment

Figure 1:
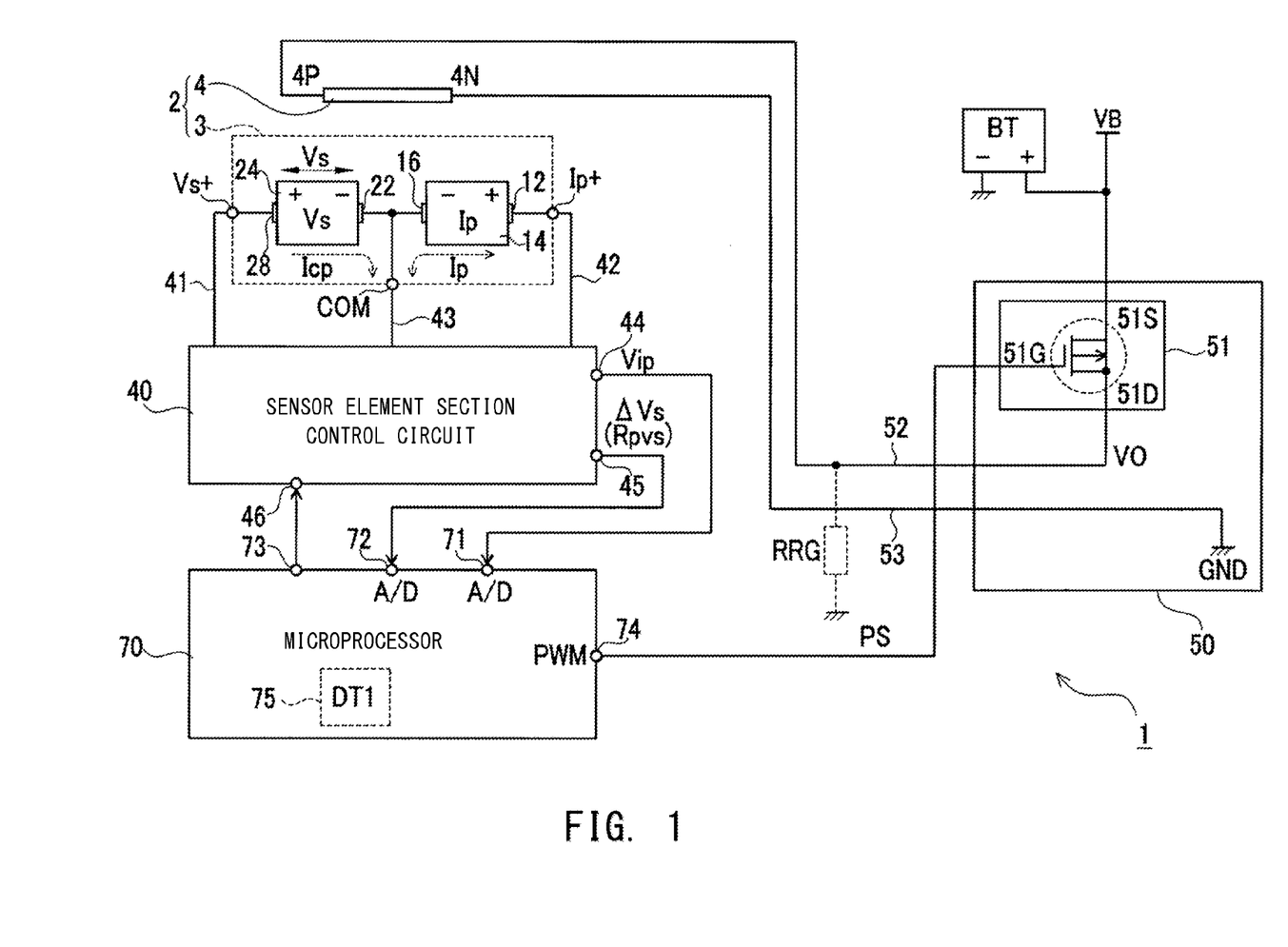
FIG. 1 Explanatory diagram schematically showing the configuration of a gas sensor control apparatus according to a first embodiment.

A first embodiment of the present invention will now be described with reference to the drawings. FIG. 1 is a diagram schematically showing the configuration of a gas sensor control apparatus 1 which is a sensor temperature control apparatus according to the present first embodiment. The gas sensor control apparatus 1 includes a microprocessor 70, a sensor element section control circuit 40, and a heater section control circuit 50, and is connected to a gas sensor 2 so as to control it.

The gas sensor 2 is an air-fuel-ratio sensor (full-range oxygen sensor) which is attached to the exhaust pipe of the internal combustion engine of an unillustrated vehicle, and detects the oxygen concentration (air-fuel ratio) of exhaust gas. The detected oxygen concentration (air-fuel ratio) is used so as to perform feedback control of air-fuel ratio for the internal combustion engine. This gas sensor 2 includes a sensor element section 3 for detecting the oxygen concentration, and a heater section 4 for heating the sensor element section 3.

The sensor element section 3 of the gas sensor 2 has a known structure in which a pump cell 14 and an electromotive force cell 24 are stacked via a spacer constituting a hollow measurement chamber (not shown) into which exhaust gas can be introduced, and an electrode located on one side of the electromotive force cell 24 opposite the measurement chamber is covered with a shield layer (not shown). Each of the pump cell 14 and the electromotive force cell 24 includes, as a substrate, a platelike, oxygen-ion-conductive solid electrolyte body mainly made of zirconia, and porous platinum electrodes 12, 16 and 22, 28 formed on opposite sides of the substrate. The electrode 16 of the pump cell 14 and the electrode 22 of the electromotive force cell 24 are electrically connected to each other and are connected to a terminal COM of the sensor element section 3. The electrode 12 of the pump cell 14 is connected to a terminal Ip+ of the sensor element section 3, and the electrode 28 of the electromotive force cell 24 is connected to a terminal Vs+ of the sensor element section 3.

The sensor element section 3 is connected to the sensor element section control circuit 40 of the gas sensor control apparatus 1 through three lead wires 41, 42, and 43 connected to the terminals Vs+, Ip+, and COM, respectively. The sensor element section control circuit 40 is mainly composed of an ASIC. While supplying a very small current Icp to the electromotive force cell 24 of the sensor element section 3, the sensor element section control circuit 40 controls the pump cell current Ip flowing through the pump cell 14 such that the electromotive force cell voltage Vs generated between the opposite ends of the electromotive force cell 24 becomes 450 mV, to thereby pump out oxygen contained in the exhaust gas introduced into the measurement chamber or pump oxygen into the measurement chamber. Since the magnitude and flow direction of the pump cell current Ip flowing through the pump cell 14 change depending on the oxygen concentration of the exhaust gas (air-fuel ratio), the concentration of oxygen contained in the exhaust gas can be calculated on the basis of the pump cell current Ip.

In the sensor element section control circuit 40, the magnitude of the pump cell current Ip is converted to an analog voltage signal, which is detected as a gas detection signal Vip and is output from an output terminal 44. Also, in addition to the gas detection signal Vip, the sensor element section control circuit 40 detects a voltage change amount ΔVs which changes in accordance with the element resistance Rpvs of the electromotive force cell 24 of the sensor element section 3. A serial transmission port 73 of the microprocessor 70 is connected to a command reception port 46 of the sensor element section control circuit 40. In response to an instruction from the microprocessor 70, the sensor element section control circuit 40 supplies a constant current to the electromotive force cell 24 temporarily, detects the voltage change amount ΔVs, and outputs it from an output terminal 45. The microprocessor 70 can receive the gas detection signal Vip and the voltage change amount ΔVs through A/D input ports 71 and 72.

The microprocessor 70 calculates the element resistance Rpvs of the electromotive force cell 24 from the voltage change amount ΔVs, and feedback-controls the energization of the heater section 4 of the gas sensor 2 through the heater section control circuit 50, which will be described next, such that the calculated element resistance Rpvs becomes equal a target resistance RT (for example, RT=75Ω). The circuit configuration and operation of the sensor element section control circuit 40 for detecting the gas detection signal Vip and the voltage change amount ΔVs are disclosed in, for example, Japanese Patent Application Laid-Open (kokai) No 2008-203190 and are well known. Therefore, the details thereof will not be described here.

Next, the heater section control circuit 50 will be described.

As shown in FIG. 1, the heater section control circuit 50 has a heater driver 51 including a power MOS-FET. A drain 51D of the heater driver 51 is connected to a power-supply-side terminal 4P of the heater section 4 of the gas sensor 2 through a lead wire 52. A source 51S of the heater driver 51 is connected to a + terminal of a power supply BT which outputs a power supply potential VB. The power supply BT is a 12 V battery.

Meanwhile, a ground-side terminal 4N of the heater section 4 is connected to the heater section control circuit 50 through a lead wire 53, and is connected to a ground potential GND within the heater section control circuit 50. Namely, the heater driver 51 is a high-side-type switching device which is interposed between the power supply BT (the power supply potential VB) and the heater section 4.

A gate 51G of the heater driver 51 is connected to a PWM output port 74 of the microprocessor 70. The heater driver 51 is turned on and off in accordance with a pulse drive signal PS output from the PWM output port 74, whereby the supply of electricity to the heater section 4 is controlled. Although not illustrated, the heater driver 51 includes a gate drive circuit for the power MOS-FET. When the pulse drive signal PS is at an "H" level, the heater driver 51 is turned on, and when the pulse drive signal PS is at an "L" level, the heater driver 51 is turned off.

The heater section 4 is united with the sensor element section 3 of the gas sensor 2. When the pump cell 14 and the electromotive force cell 24 of the sensor element section 3 are activated as a result of heating by the heater section 4, detection of the oxygen concentration becomes possible.

When electricity is supplied to the heater section 4, as indicted by a broken line in FIG. 1, the lead wire 52 which connects the drain 51D of the heater driver 51 and the power-supply-side terminal 4P of the heater section 4 may communicate (conduct) with the ground potential GND through a resistive short circuit RRG whose resistance is somewhat large. As a result, only a portion of the current flowing through the heater driver 51 flows through the heater section 4, and the remaining portion of the current flows through the resistive short circuit RRG (hereinafter, this state will be also referred to as a "semi-shorted state").

In the below, the case where the lead wire 52 is semi-shorted to the ground potential GND in a state in which the energization control of the heater section 4 is being performed such that the element resistance Rpvs becomes equal to the target resistance RT (RT=75Ω) will be considered with reference to the timing chart of FIG. 2. Notably, the timing chart of FIG. 2 represents a case where the lead wire 52 is semi-shorted to the ground potential GND in a state in which the internal combustion engine operates stably.

Figure 2:
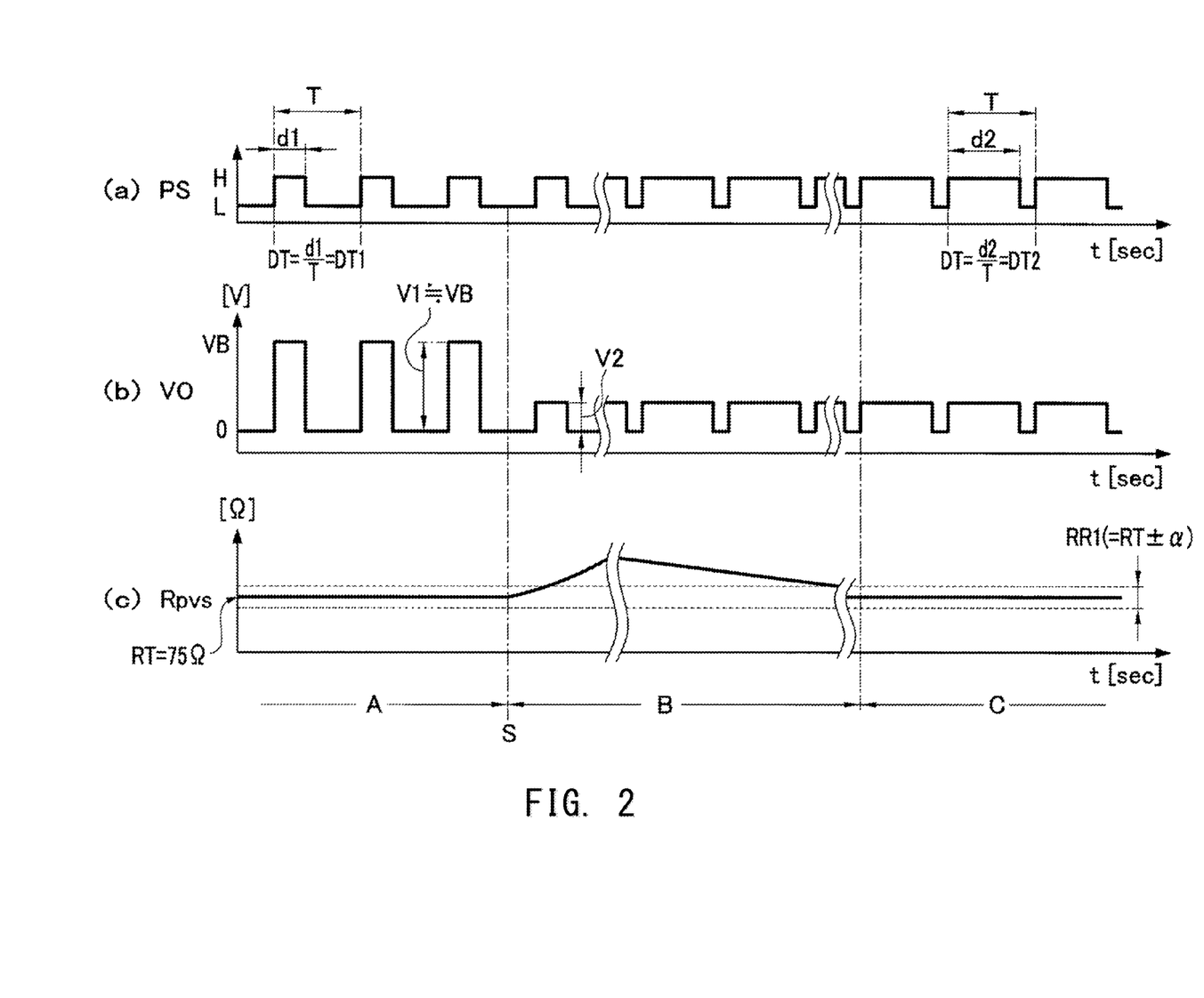
FIG. 2 Timing chart showing a pulse drive signal, the voltage at an output terminal of a heater driver, and the element resistance of a sensor element section in the gas sensor control apparatus according to the first embodiment.

In FIG. 2, section (a) shows the pulse drive signal PS [H or L] output from the PWM output port 74 of the microprocessor 70, section (b) shows an output end voltage VO [V], which is the voltage level of the drain 51D of the heater driver 51, and section (c) shows the element resistance Rpvs [Ω] of the sensor element section 3 (the electromotive force cell 24). The horizontal axis common to the sections (a) to (c) represents time t [sec].

During a period A shown in FIG. 2, any resistive short circuit RRG is not formed, and all the current flowing through the heater driver 51 flows through the heater section 4 (hereinafter, this state will also be referred to as an "un-shorted state"). The energization control of the heater section 4 is normally performed such that the element resistance Rpvs becomes equal to the target resistance RT (RT=75Ω), whereby the sensor element section 3 is maintained at the target temperature corresponding to the target resistance RT (specifically, a temperature within a first temperature range to be described later which includes the target temperature). Namely, during the period A, all the current flowing through the heater driver 51 flows through the heater section 4 (the un-shorted state) and the sensor element section 3 is maintained at the target temperature (this state will be referred to as an "un-shorted constant temperature state"). The duty ratio DT (the ratio of the on period d1 of the pulse drive signal PS to the period T thereof) of the pulse drive signal PS in the un-shorted constant temperature state will be referred to as a first duty ratio DT1 (DT=DT1 (=d1/T)). In this un-shorted constant temperature state, when the heater driver 51 is turned on, the output end voltage (pulse voltage) VO becomes V1 which is approximately equal to the power supply potential VB (V1≅VB).

Next, there is assumed that, at time t=S of FIG. 2, the lead wire 52 communicates with the ground potential GND through a resistive short circuit RRG having a resistance as indicated by a broken line in FIG. 1, whereby a semi-shorted state is established. In the semi-shorted state, as described previously, only a portion of the current flowing through the heater driver 51 flows through the heater section 4, and the remaining portion of the current flows through the resistive short circuit RRG. Therefore, if the current flowing from the heater driver 51 to the heater section 4 and the resistive short circuit RRG when the heater driver 51 is turned on reaches the upper limit of the current which can flow through the heater driver 51, the current flowing through the heater driver 51 is limited, whereby the height (magnitude) of the output end voltage (pulse voltage) VO decreases from V1 to V2.

Thus, during a period B of FIG. 2, the electric power supplied to the heater section 4 decreases as a result of the drop of the output end voltage VO, whereby the temperature of the sensor element section 3 decreases, and the element resistance Rpvs increases. However, since feedback control is performed such that the element resistance Rpvs becomes equal to the target resistance RT (RT=75Ω), as shown in the second half of the period B, the duty ratio DT of the pulse drive signal PS is increased. As a result, the temperature of the sensor element section 3 again increases, and the element resistance Rpvs decreases. Thus, as shown in a period C, despite the semi-shorted state, the sensor element section 3 again becomes stable in a state in which the element resistance Rpvs becomes equal to the target resistance RT (specifically, a resistance within a first resistance range RR1 (the target resistance RT±α) which includes the target resistance RT and which corresponds to the first temperature range), and the sensor element section 3 maintains the target temperature (specifically, a temperature within the first temperature range which includes the target temperature) (semi-shorted first temperature range state). Notably, the duty ratio DT (the ratio of the on period d2 of the pulse drive signal PS to the period T thereof) of the pulse drive signal PS during the period C in the semi-shorted first temperature range state has occurred) will be referred to as a present duty ratio DT2 (DT=DT2(=d2/T)). The present duty ratio DT2 is larger than the first duty ratio DT1 in the un-shorted constant temperature state.

Notably, even in the semi-shorted state in which only a portion of the current flowing through the heater driver 51 flows through the heater section 4, the phenomenon as shown in the period C of FIG. 2 does not occur in some simulations. Rather, the output end voltage VO greatly decreases, the temperature of the sensor element section 3 decreases, and even when the duty ratio DT is increased to the upper limit (near 100%), the sensor element section 3 cannot maintain a temperature within the first temperature range which includes the target temperature (the element resistance Rpvs=the target resistance RT±α). In such a case, it can be determined that some anomaly has occurred on the basis of the fact that the sensor element section 3 cannot maintain a temperature within the first temperature range. However, in the semi-shorted first temperature range state in which, despite the semi-shorted state, the element resistance Rpvs becomes equal to a resistance within a first resistance range RR1 (the target resistance RT±α) and the sensor element section 3 maintains a temperature within the first temperature range which includes the target temperature as shown in the period C of FIG. 2, the energization control of the heater section 4 is continued in a state in which occurrence of an anomaly cannot be detected. If the energization is continued in the semi-shorted first temperature range state, the upper limit current continuously flows through the heater driver 51. Therefore, energy is wasted, and the heater driver 51 may fail.

In view of the above problem, in the gas sensor control apparatus 1 of the present first embodiment, the first duty ratio DT1 (fixed value)—which is a duty ratio DT in the un-shorted constant temperature state in which all the current flowing through the heater driver 51 flows through the heater section 4, the element resistance Rpvs becomes equal to the target resistance RT, and the sensor element section 3 is maintained at the target temperature—is stored in a nonvolatile memory 75 in advance. The stored first duty ratio DT1 is compared with the present duty ratio DT2—which is the present duty ratio DT of the pulse drive signal PS output from the PWM output port 74 of the microprocessor 70—in a state in which the element resistance Rpvs becomes equal to a resistance (50 to 100Ω) within the first resistance range RR1 (the element resistance Rpvs=the target resistance RT±α (e.g., α=25Ω)) and the sensor element section 3 maintains a temperature within the first temperature range including the target temperature. In the case where the present duty ratio DT2 is sufficiently greater than the first duty ratio DT1; specifically, in the case where a value obtained by subtracting the first duty ratio DT1 from the present duty ratio DT2 is greater than a predetermined threshold value, the gas sensor control apparatus 1 determines that there has arisen the semi-shorted first temperature range state in which the lead wire 52 communicates with the ground potential GND through the resistive short circuit RRG having a resistance.

As a result, in a state in which the sensor element section 3 is maintained at a temperature within the first temperature range including the target temperature, it is possible to properly determine whether or not the gas sensor 2, the gas sensor control apparatus 1, and the resistive short circuit RRG are in the semi-shorted first temperature range state.

Next, processing of detecting the semi-shorted first temperature range state performed by the microprocessor 70 of the gas sensor control apparatus 1 according to the present first embodiment will be described with reference to the flowchart of FIG. 3.

Figure 3:
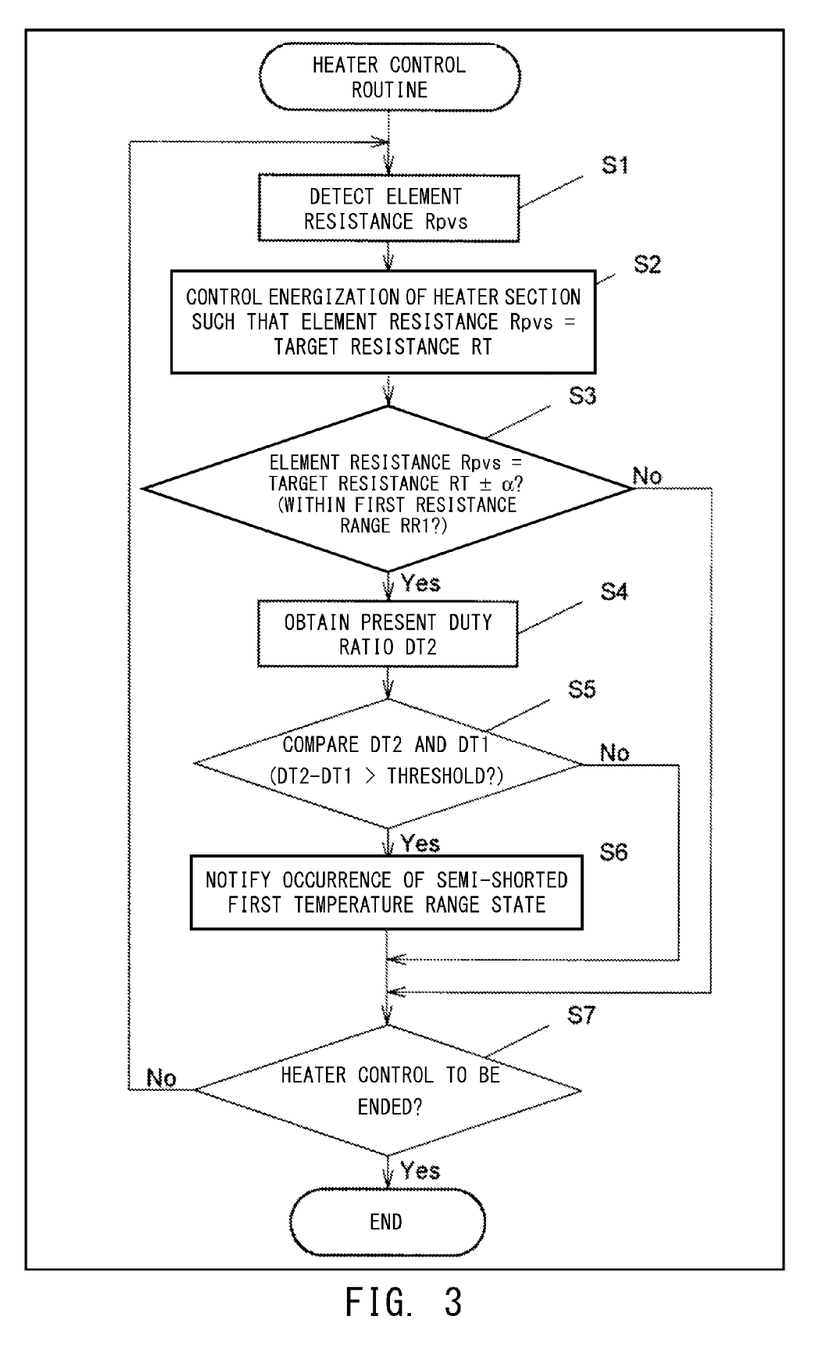
FIG. 3 Flowchart showing heater control processing and processing of determining occurrence of a semi-shorted, first temperature range state, which are performed by a microprocessor in the gas sensor control apparatus of the first embodiment and in a gas sensor control apparatus of a second embodiment.

In the present first embodiment, as shown in FIG. 3, the processing of detecting the semi-shorted first temperature range state is performed in a heater control routine for energizing and controlling the heater section 4.

First, in step S1, the microprocessor 70 detects (calculates) the element resistance Rpvs from the voltage change amount ΔVs which is output from the output terminal 45 of the sensor element section control circuit 40 and is input to the microprocessor 70 through the A/D input port 72. In step S2 subsequent thereto, the microprocessor 70 feedback-controls the energization of the heater section 4 through the heater section control circuit 50 such that the detected element resistance Rpvs becomes equal to the target resistance RT (=75Ω).

Next, in step S3, the microprocessor 70 determines whether or not the detected element resistance Rpvs becomes equal to a resistance within the first resistance range RR1 including the target resistance RT (=75Ω) (the element resistance Rpvs=the target resistance RT±α (e.g., α=25Ω)).

In the case where the element resistance Rpvs does not become equal to a resistance (50 to 100Ω) within the first resistance range RR1 (No), the microprocessor 70 proceeds to step S7 while skipping steps for detecting the semi-shorted first temperature range state. Meanwhile, in the case where the element resistance Rpvs becomes equal to a resistance (50 to 100Ω) within the first resistance range RR1 (Yes), the microprocessor 70 proceeds to step S4, and performs the steps for detecting the semi-shorted first temperature range state.

In step S4, the microprocessor 70 obtains the present duty ratio DT2 of the pulse drive signal PS output from the PWM output port 74 of the microprocessor 70.

Next, in step S5, the microprocessor 70 compares the present duty ratio DT2 obtained in step S4 with the first duty ratio DT1 stored in the nonvolatile memory 75. Specifically, the microprocessor 70 substrates the first duty ratio DT1 from the present duty ratio DT2, and determines whether or not the resultant value (DT2−DT1) is greater than a predetermined threshold value. In the case where the resultant value (DT2−DT1) is greater than the threshold value (Yes), the microprocessor 70 proceeds to step S6.

In step S6, the microprocessor 70 determines that the lead wire 52 communicates with the ground potential GND through the resistive short circuit RRG having a resistance and the semi-shorted first temperature range state has occurred, and notifies an external device (ECU) of occurrence of the semi-shorted first temperature range state.

In step S7 subsequent thereto, the microprocessor 70 checks where or not a heater control end instruction is sent from the external device (ECU). When the end instruction is not sent (No), the microprocessor 70 returns to step S1 and continues the energization control for the heater section 4. Meanwhile, in the case where the heater control end instruction is sent from the external device (Yes), the microprocessor 70 ends the present heater control routine.

In the present first embodiment, the heater driver 51 corresponds to the switching device. The heater section control circuit 50 (including the heater driver 51), the PWM output port 74, the sensor element section control circuit 40, the A/D input port 72, and the microprocessor 70 which executes steps S1 and S2 correspond to the energization control means. Of the energization control means, the sensor element section control circuit 40, the A/D input port 72, and the microprocessor 70 which executes step S1 correspond to the element resistance detection means, and the microprocessor 70 which executes step S2 corresponds to the element resistance control means.

The nonvolatile memory 75 corresponds to the storage means, and the microprocessor 70 which executes step S3 corresponds to the element resistance judgment means (the element temperature judgment means). The microprocessor 70 which executes steps S4 to S6 corresponds to the semi-shorted state detection means, and the microprocessor 70 which executes step S6 corresponds to the first judgment means.

The lead wire 52 which connects the drain 51D of the heater driver 51 and the power-supply-side terminal 4P of the heater section 4 corresponds to the first connection path.

As having been described, in the gas sensor control apparatus 1 which is the sensor temperature control apparatus of the present first embodiment, the first duty ratio DT1 which is the duty ratio DT in the un-shorted constant temperature state (in which all the current flowing through the heater driver 51 flows through the heater section 4 (un-shorted state) and the sensor element section 3 is maintained at the target temperature) is stored in the nonvolatile memory 75 (storage means) in advance.

The first duty ratio DT1 stored in advance is compared with the present duty ratio DT2 in a state in which the element resistance Rpvs becomes equal to a resistance within the first resistance range RR1 including the target resistance RT (the element resistance Rpvs=the target resistance RT±α (50 to 100Ω)) (when the result of the determination in step S3 is Yes). Thus, the determination as to whether or not the semi-shorted first temperature range state has occurred can be made.

As a result, the determination as to whether or not the semi-shorted first temperature range state has occurred can be made properly in a state in which the sensor element section 3 is maintained at a temperature within the first temperature range including the target temperature.

Further, in the gas sensor control apparatus 1 of the present first embodiment, the heater driver 51 is a high-side-type switching device disposed between the power supply BT (the power supply potential VB) and the heater section 4. The semi-shorted state detection means includes the first judgment means, and compares the present duty ratio DT2 with the first duty ratio DT1 to thereby determines whether or not the lead wire 52 (the first connection path) which connects the drain 51D of the heater driver 51 and the power-supply-side terminal 4P of the heater section 4 communicates with the ground potential GND through the resistive short circuit RRG having a resistance, and the gas sensor 2, the gas sensor control apparatus 1, and the resistive short circuit RRG are in the semi-shorted first temperature range state. As a result, occurrence of the semi-shorted first temperature range state can be determined properly in the gas sensor control apparatus 1 which is a sensor temperature control apparatus using a high-side type switching device.

In the gas sensor control apparatus 1 of the present first embodiment, the energization control means (steps S1 and S2) includes the element resistance detection means (step S1) and the element resistance control means (step S2), and feedback-controls the duty ratio DT of the energization pulse PS such that the detected element resistance Rpvs becomes equal to the target resistance RT corresponding to the target temperature. Also, the element resistance judgment means (step S3) which is the element temperature judgment means determines whether or not the element resistance Rpvs becomes equal to a resistance within the first resistance range RR1 which includes the target resistance RT and which corresponds to the first temperature range (the element resistance Rpvs=the target resistance RT±α (50 to 100Ω)). The semi-shorted state detection means (steps S4 to S6) determines whether or not the semi-shorted first temperature range state has occurred, in a state in which the element resistance Rpvs becomes equal to a resistance (50 to 100Ω) within the first resistance range RR1.

As a result, the semi-shorted first temperature range state can be detected properly through use of the element resistance Rpvs.

Second Embodiment

Next, a second embodiment of the present invention will be described with reference to FIG. 4. In the gas sensor control apparatus 1 which is the sensor embodiment, the heater driver 51 provided in the heater section control circuit 50 is a high-side-type switching device interposed between the power supply BT (the power supply potential VB) and the heater section 4.

In contrast, in a gas sensor control apparatus 1A which is a sensor temperature control apparatus according to the present second embodiment, a heater driver 151 provided in a heater section control circuit 150 is a low-side-type switching device interposed between the heater section 4 and the ground potential GND.

Figure 4:
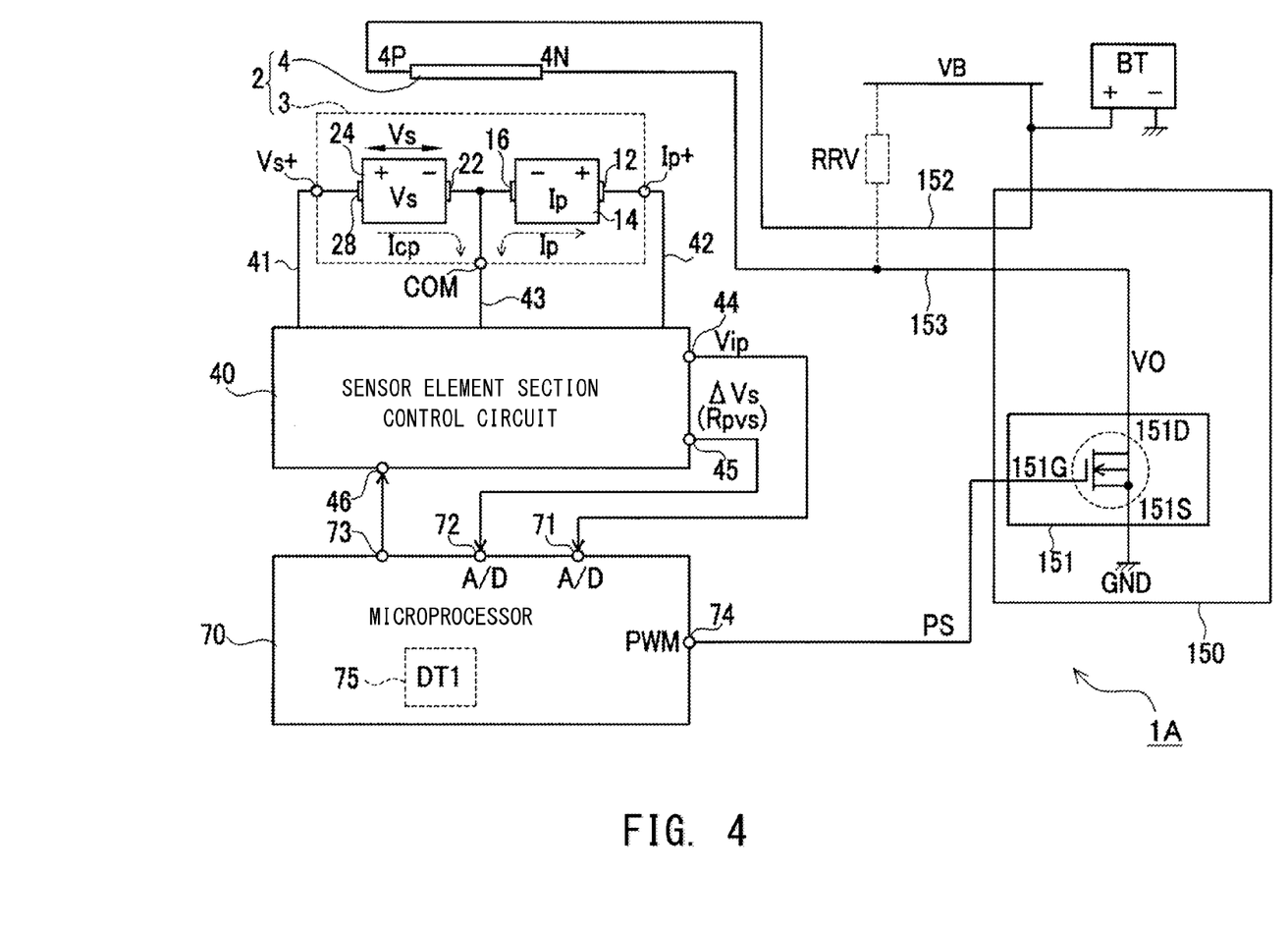
FIG. 4 Explanatory diagram schematically showing the configuration of the gas sensor control apparatus according to the second embodiment.

As shown in FIG. 4, the heater section control circuit 150 has the heater driver 151 including a power MOS-FET. A drain 151D of the heater driver 151 is connected to the ground-side terminal 4N of the heater section 4 of the gas sensor 2 through a lead wire 153. A source 151S of the heater driver 151 is connected to the ground potential GND.

Meanwhile, the power-supply-side terminal 4P of the heater section 4 is connected to the heater section control circuit 150 through a lead wire 152, and is connected, within the heater section control circuit 150, to the + terminal of the power supply BT which outputs the power supply potential VB. Notably, the power supply BT is a 12 V battery. Namely, the heater driver 151 is a low-side-type switching device which is interposed between the heater section 4 and the ground potential GND.

A gate 151G of the heater driver 151 is connected to the PWM output port 74 of the microprocessor 70. The heater driver 151 is turned on and off in accordance with the pulse drive signal PS output from the PWM output port 74, whereby the supply of electricity to the heater section 4 is controlled.

In the gas sensor control apparatus 1A of the present second embodiment, when electricity is supplied to the heater section 4, as indicted by a dotted line in FIG. 4, the lead wire 153 which connects the drain 151D of the heater driver 151 and the ground-side terminal 4N of the heater section 4 may communicate (conduct) with the power supply potential VB through a resistive short circuit RRV having a resistance. As a result, only a portion of the current flowing through the heater driver 151 flows through the heater section 4, and the remaining portion of the current flows through the resistive short circuit RRV. Namely, the above-described semi-shorted state occurs.

In view of the above problem, in the gas sensor control apparatus 1A of the present second embodiment, the first duty ratio DT1 (fixed value) is stored in a nonvolatile memory 75 in advance as in the case of the first embodiment. The stored first duty ratio DT1 is compared with the present duty ratio DT2—which is the present duty ratio DT of the pulse drive signal PS output from the PWM output port 74 of the microprocessor 70—in a state in which the element resistance Rpvs becomes equal to a resistance (50 to 100Ω) within the first resistance range RR1 (the element resistance Rpvs=the target resistance RT±α) and the sensor element section 3 maintains a temperature within the first temperature range including the target temperature. In the case where the present duty ratio DT2 is sufficiently greater than the first duty ratio DT1; specifically, in the case where a value obtained by subtracting the first duty ratio DT1 from the present duty ratio DT2 is greater than a predetermined threshold value, the gas sensor control apparatus 1A determines that there has occurred a semi-shorted first temperature range state in which the lead wire 153 communicates with the power supply potential VB through the resistive short circuit RRV having a resistance.

As a result, in a state in which the sensor element section 3 is maintained at the target temperature, it is possible to properly determine whether or not the gas sensor 2, the gas sensor control apparatus 1A, and the resistive short circuit RRV are in the semi-shorted first temperature range state.

The processing of detecting the semi-shorted first temperature range state performed by the microprocessor 70 of the gas sensor control apparatus 1A according to the present second embodiment is the same as that in the first embodiment shown by the flowchart of FIG. 3.

In the present second embodiment, in step S6, the microprocessor 70 can determine that the lead wire 153 communicates with the power supply potential VB through the resistive short circuit RRV having a resistance and the semi-shorted first temperature range state has occurred, and notifies the external device (ECU) of occurrence of the semi-shorted first temperature range state.

In the present second embodiment, the heater driver 151 corresponds to the switching device. The heater section control circuit 150 (including the heater driver 151), the PWM output port 74, the sensor element section control circuit 40, the A/D input port 72, and the microprocessor 70 which executes steps S1 and S2 correspond to the energization control means. Of the energization control means, the sensor element section control circuit 40, the A/D input port 72, and the microprocessor 70 which executes step S1 correspond to the element resistance detection means, and the microprocessor 70 which executes step S2 corresponds to the element resistance control means.

The nonvolatile memory 75 corresponds to the storage means, and the microprocessor 70 which executes step S3 corresponds to the element resistance judgment means (the element temperature judgment means). The microprocessor 70 which executes steps S4 to S6 corresponds to the semi-shorted state detection means, and the microprocessor 70 which executes step S6 corresponds to the second judgment means.

The lead wire 153 which connects the drain 151D of the heater driver 151 and the ground-side terminal 4N of the heater section 4 corresponds to the second connection path.

As having been described, in the gas sensor control apparatus 1A which is the sensor temperature control apparatus of the present second embodiment, the determination as to whether or not the semi-shorted first temperature range state has occurred is made in the same manner as in the gas sensor control apparatus 1 of the first embodiment. Specifically, the determination is made by comparing the first duty ratio DT1 stored in advance with the present duty ratio DT2 in a state in which the element resistance Rpvs becomes equal to a resistance within the first resistance range RR1 including the target resistance RT (the element resistance Rpvs=the target resistance RT±α (50 to 100Ω)).

As a result, as in the case of the first embodiment, the determination as to whether or not the semi-shorted first temperature range state has occurred can be made properly in a state in which the sensor element section 3 is maintained at a temperature within the first temperature range including the target temperature.

Further, in the gas sensor control apparatus 1A of the present second embodiment, the heater driver 151 is a low-side-type switching device disposed between the heater section 4 and the ground potential GND. The semi-shorted state detection means includes the second judgment means, and compares the present duty ratio DT2 with the first duty ratio DT1 to thereby determines whether or not the lead wire 153 (the second connection path) which connects the drain 151D of the heater driver 151 and the ground-side terminal 4N of the heater section 4 communicates with the power supply potential VB through the resistive short circuit RRV having a resistance, and the gas sensor 2, the gas sensor control apparatus 1A, and the resistive short circuit RRV are in the semi-shorted first temperature range state. As a result, occurrence of the semi-shorted first temperature range state can be determined properly in the gas sensor control apparatus 1A which is a sensor temperature control apparatus using a low-side type switching device.

In the gas sensor control apparatus 1A of the present second embodiment, as in the case of the first embodiment, the energization control means (steps S1 and S2) includes the element resistance detection means (step S1) and the element resistance control means (step S2), and feedback-controls the duty ratio DT of the energization pulse PS such that the detected element resistance Rpvs becomes equal to the target resistance RT corresponding to the target temperature. Also, the element resistance judgment means (step S3) which is the element temperature judgment means determines whether or not the element resistance Rpvs becomes equal to a resistance within the first resistance range RR1 which includes the target resistance RT and which corresponds to the first temperature range (the element resistance Rpvs=the target resistance RT±α (50 to 100Ω)). The semi-shorted state detection means (steps S4 to S6) determines whether or not the semi-shorted first temperature range state has occurred, in a state in which the element resistance Rpvs becomes equal to a resistance (50 to 100Ω) within the first resistance range RR1.

As a result, the semi-shorted first temperature range state can be detected properly through use of the element resistance Rpvs.

In the above, the sensor temperature control apparatus of the present invention has been described on the basis of the gas sensor control apparatuses 1 and 1A of the first and second embodiments. However, needless to say, the present invention is not limited to the above-described embodiments, and may be modified freely without departing from the scope of the invention.

For example, in the first and second embodiments, the gas sensor 2 which is an air-fuel ratio sensor for detecting the concentration of oxygen contained in exhaust gas (air-fuel ratio) is used as a sensor having a sensor element section and a heater section. However, the sensor having a heater section is not limited to the air-fuel ratio sensor, and may be an oxygen sensor for detecting whether or not the concentration of oxygen is high or low (rich/lean), an NOx sensor for detecting the concentration of nitrogen oxide (NOx), or the like.

Also, in the first and second embodiments, a fixed value is stored in the nonvolatile memory 75 (storage means) as the first duty ratio DT1, and is used continuously. However, the embodiments may be modified such that a normal duty ratio DT in the un-shorted constant temperature state obtained in the previous operation is stored as the first duty ratio DT1, and is used at the time of the next operation. Use of the duty ratio DT at the time of the previous operation allows the first duty ratio DT1 to change in accordance with a change in the element resistance Rpvs, which change occurs due to deterioration or the like.

DESCRIPTION OF SYMBOLS

1, 1A: gas sensor control apparatus (sensor temperature control apparatus)
2: gas sensor
3: sensor element section
4: heater section
4P: power-supply-side terminal
4N: ground-side terminal
Rpvs: element resistance
RT: target resistance
40: sensor element section control circuit (element resistance detection means, energization control means)
50, 150: heater section control circuit (energization control means)
51, 151: heater driver (switching device)
52, 152: lead wire (first connection path)
53, 153: lead wire (second connection path)
70: microprocessor
72: A/D input port (element resistance detection means, energization control means)
74: PWM output port (energization control means)
75: nonvolatile memory (storage means)
BT: power supply (battery)
PS: pulse drive signal
DT: duty ratio
DT1: first duty ratio
DT2: present duty ratio
RR1: first resistance range
S1: element resistance detection means (energization control means)
S2: element resistance control means (energization control means)
S3: element resistance judgment means (element temperature judgment means)
S4 to S6: semi-shorted state detection means
S6: first judgment means, second judgment means

The invention claimed is:

1. A sensor temperature control apparatus used for a sensor having a sensor element section and a heater section for heating the sensor element section and adapted to control temperature of the sensor element section by controlling pulse energization of the heater section, the sensor temperature control apparatus comprising:
a switching device which allows and prohibits supply of electricity to the heater section;
energization control means for feedback-controlling a duty ratio of an energization control pulse signal input to the switching device such that the sensor element section is maintained at a target temperature;
storage means for storing in advance a first duty ratio which is the duty ratio in an un-shorted constant temperature state in which all current flowing through the switching device flows through the heater section and the sensor element section is maintained at the target temperature;
element temperature judgment means for determining whether or not the temperature of the sensor element section falls within a first temperature range including the target temperature; and
semi-shorted state detection means for comparing a present duty ratio which is the duty ratio at present with the previously stored first duty ratio in a state in which the temperature of the sensor element section falls within the first temperature range, to thereby determine whether or not there has arisen a semi-shorted first temperature range state in which only a portion of the current flowing through the switching device flows through the heater section and the temperature of the sensor element section falls within the first temperature range.

2. The sensor temperature control apparatus as claimed in claim 1, wherein
the switching device is a high-side-type switching device interposed between a power supply potential and the heater section; and
the semi-shorted state detection means includes first judgment means for determining, by comparing the present duty ratio with the first duty ratio, whether or not a first connection path which connects the switching device and a power-supply-side terminal of the heater section communicates with a ground potential through a resistive short circuit having a resistance, and the semi-shorted first temperature range state has arisen.

3. The sensor temperature control apparatus as claimed in claim 1, wherein
the switching device is a low-side-type switching device interposed between the heater section and a ground potential; and
the semi-shorted state detection means includes second judgment means for determining, by comparing the present duty ratio with the first duty ratio, whether or not a second connection path which connects a ground-side terminal of the heater section and the switching device communicates with a power supply potential through a resistive short circuit having a resistance, and the semi-shorted first temperature range state has arisen.

4. The sensor temperature control apparatus as claimed in claim 1, wherein
the sensor element section has a characteristic that its element resistance changes with its temperature;
the energization control means includes element resistance detection means for detecting the element resistance of the sensor element section, and element resistance control means for feedback-controlling the duty ratio such that the detected element resistance becomes equal to a target resistance;
the element temperature judgment means is element resistance judgment means for determining whether or not the element resistance falls within a first resistance range including the target resistance; and
the semi-shorted state detection means is means for determining whether or not the semi-shorted first temperature range state has arisen by comparing the present duty ratio with the first duty ratio in a state in which the element resistance falls within the first resistance range.

* * * * *